(12) United States Patent
Beselt et al.

(10) Patent No.: US 7,599,582 B2
(45) Date of Patent: Oct. 6, 2009

(54) OPTICAL FIBER CABLE TAKE-UP MECHANISM FOR SCANNING SENSORS

(75) Inventors: Ronald E. Beselt, Burnaby (CA); Frank M. Haran, North Vancouver (CA); John A. Harjula, North Vancouver (CA); Ulysse S. Dos Santos, Burnaby (CA)

(73) Assignee: Honeywell International Inc., Morristown, NJ (US)

( * ) Notice: Subject to any disclaimer, the term of this patent is extended or adjusted under 35 U.S.C. 154(b) by 1201 days.

(21) Appl. No.: 10/994,862

(22) Filed: Nov. 22, 2004

(65) Prior Publication Data

US 2006/0109519 A1    May 25, 2006

(51) Int. Cl.
G02B 6/00 (2006.01)
G01B 11/16 (2006.01)
G01J 3/00 (2006.01)
G01N 21/84 (2006.01)

(52) U.S. Cl. .......... 385/13; 385/12; 385/134; 356/35; 356/36; 356/51; 356/431

(58) Field of Classification Search .......... 385/12, 385/13, 134; 356/35, 36, 51, 238.1, 431; 358/474, 484, 497
See application file for complete search history.

(56) References Cited

U.S. PATENT DOCUMENTS

| | | | |
|---|---|---|---|
| 4,343,991 A | 8/1982 | Fujiwara et al. | |
| 4,688,555 A | 8/1987 | Wardle | 128/4 |
| 4,830,503 A | 5/1989 | Hoda et al. | |
| 4,879,471 A | 11/1989 | Dahlquiest | |
| 4,893,786 A | 1/1990 | Huber | 254/414 |
| 4,953,804 A | 9/1990 | Hester | 242/47 |
| 4,954,834 A | 9/1990 | Buck | 342/360 |
| 5,094,535 A | 3/1992 | Dahlquist et al. | 356/346 |
| 5,166,748 A | 11/1992 | Dahlquist | 356/346 |
| 5,170,056 A | 12/1992 | Berard et al. | 250/341 |
| 5,277,928 A | 1/1994 | Strandberg | 427/10 |
| 5,343,296 A | 8/1994 | Hellstrom | |
| 5,391,071 A | 2/1995 | Hazarie et al. | 425/135 |
| 5,452,393 A | 9/1995 | Stowe et al. | 385/123 |
| 5,596,668 A | 1/1997 | DiGiovanni et al. | 385/123 |

(Continued)

FOREIGN PATENT DOCUMENTS

DE    29709504    7/1997

(Continued)

Primary Examiner—Uyen Chau N Le
Assistant Examiner—Rhonda S Peace
(74) Attorney, Agent, or Firm—Cascio, Schmoyer, & Zervas (57) ABSTRACT

A scanning system includes a cable take-up mechanism that uses a series of pulleys that determine the bend diameters of a scanning system. The mechanism is particularly suited for a spectrometric, e.g., infrared, scanning system where moving scanner or sensor head essentially houses only the optical elements while essentially of all the other electronic and optical components associated with the measurement are housed in an easily accessible compartment that is remote from the moving scanner head. Light is transmitted through optical fiber cables. The cable take-up mechanism maintains the fiber optic cable at essentially constant total bend length and bend diameter thereby minimizing any dynamic changes to spectral bend losses as the optical head is scanned. The light weight construction of the sensor head further reduces vibrations associated with the moving scanner head.

28 Claims, 5 Drawing Sheets

U.S. PATENT DOCUMENTS

| | | | |
|---|---|---|---|
| 5,717,503 A * | 2/1998 | Chien | 358/475 |
| 5,764,839 A | 6/1998 | Igl et al. | 385/114 |
| 5,779,376 A * | 7/1998 | Seu | 400/335 |
| 5,795,394 A | 8/1998 | Belotserkovsky et al. | 118/665 |
| 6,134,370 A | 10/2000 | Childers et al. | 385/134 |
| 6,271,476 B1 | 8/2001 | Bobowick et al. | 174/135 |
| 6,404,502 B2 | 6/2002 | Preston | 356/445 |
| 6,504,094 B2 | 1/2003 | Woo et al. | 174/50 |
| 6,535,681 B2 | 3/2003 | Daoud et al. | 385/134 |
| 6,595,454 B2 | 7/2003 | Roba et al. | 242/412.2 |
| 6,603,918 B2 | 8/2003 | Daoud et al. | 385/134 |
| 6,674,952 B2 | 1/2004 | Howell et al. | 385/135 |
| 6,678,455 B1 | 1/2004 | Knight | 385/134 |
| 6,678,456 B2 | 1/2004 | Etemad-Moghadam | 385/134 |
| 6,726,309 B2 | 4/2004 | Maki | 347/50 |
| 7,291,856 B2 * | 11/2007 | Haran et al. | 250/574 |

FOREIGN PATENT DOCUMENTS

| | | |
|---|---|---|
| EP | 0390623 | 10/1990 |
| WO | WO 03/037111 | 5/2003 |

* cited by examiner

OPTICAL FIBER CABLE TAKE-UP MECHANISM FOR SCANNING SENSORS

FIELD OF THE INVENTION

The present invention generally relates to an apparatus for routing moving flexible cables wherein the radius of curvature of the cable and the nominal total bend length is maintained and to a device that controls the optical fiber path through a series of bends that do not change in number or diameter even as the optical fiber is moved back and forth along a defined linear path.

BACKGROUND OF THE INVENTION

It is often desirable to obtain measurements of selected characteristics of sheet materials during manufacture. Although various properties of sheet materials can be detected by off-line laboratory testing, such tests often are not practical because of the time required for sample acquisition and analysis. Also, laboratory testing has the shortcoming that samples obtained for testing may not accurately represent sheet material that has been produced.

To overcome the drawbacks of laboratory testing of sheet materials, various sensor systems have been used for detecting sheet properties "on-line," i.e., on a sheet-making machine while it is operating. Typically, on-line sensor devices are operated to periodically traverse, or "scan," traveling webs of sheet material during manufacture. Scanning usually is done in the cross direction, i.e., in the direction perpendicular to the direction of sheet travel. Depending upon the sheet-making operation, cross-directional distances can range up to about 10 meters or more.

Figure 6A:
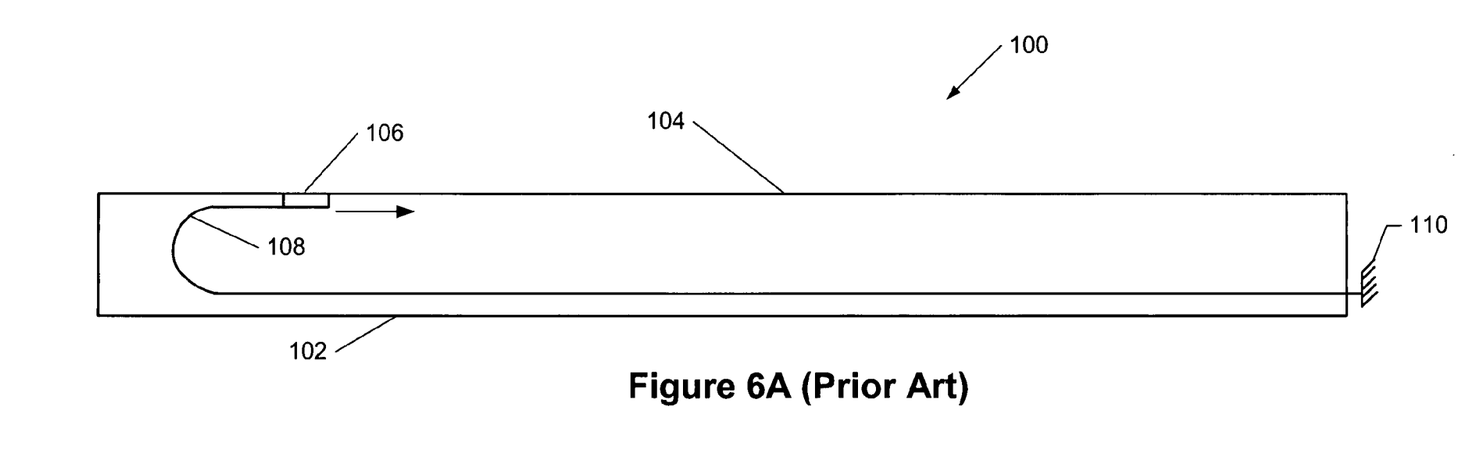
FIGS. 6A and 6B are side schematic views of a prior art scanning system.
Figure 6B:
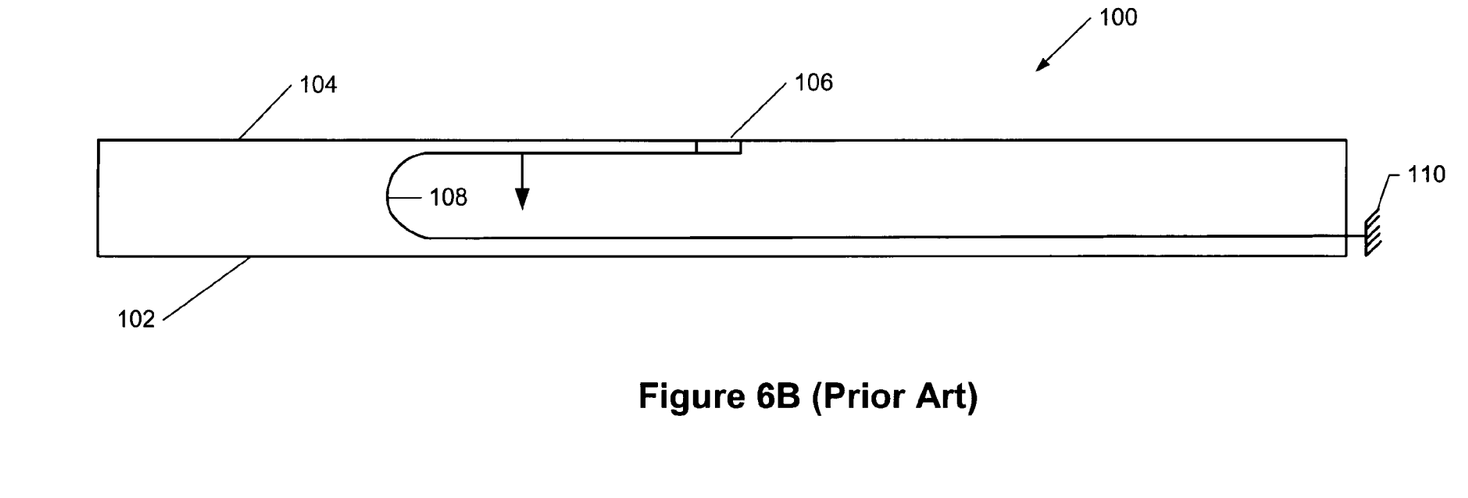

A wide variety of scanning sensor devices have been used for on-line measurements of sheet materials. As illustrated in FIGS. 6A and 6B, the scanning sensor system 100 typically includes a stationary frame 102, having a pair of upright end members that stand on a factory floor for supporting a guide member 104 that extends horizontally across a traveling sheet (not shown). A motor driven carriage is mounted to travel on the guide member 104. The carriage is connected to a drive system to be driven back and forth across sheet. The scanning sensor system also includes a scanning head 106 that is mounted on the carriage member. The scanning head 106 contains the detection components. For example, in the case of a spectrometric analyzer, the scanner head can include a source of infrared light, collimating and beam-splitting mirrors, and photosensitive detector.

The scanner head 106 is electronically connected by a wire 108 that is connected to the process controller 110. The scanner head 106 travels back and forth along the cross direction adjacent the traveling sheet being analyzed. In FIG. 6A, the scanner head 106 is at one side of the frame 102 and is moving toward the middle of the frame 102 as shown in FIG. 6B. As is apparent, gravity causes the suspended wire 108 to sag because of the lack of adequate support.

With prior art scanning sensors, the detection components, that are located in the scanner head, are subject to vibrations as the carriage moves back and forth. Moreover, the presence of the relatively heavy detection components in the scanning head makes it more difficult to drive the carriage and to control its speed. These phenomena combined to reduce the precision and accuracy of the detectors. Finally, the inclusion of the detection components within the scanner head makes them less accessible; indeed, the carriage must be stopped and the scanner head disassembled whenever the detection components need to be inspected.

SUMMARY OF THE INVENTION

The present invention is based in part on the recognition that various performance advantages can be achieved by developing a spectrometric, e.g., infrared, scanning system where the weight of the moving scanner or sensor head is minimized. In a preferred embodiment, this is achieved by designing a moving scanner head that essentially houses some of the optical elements while essentially of all the other electronic and optical elements associated with the measurement are housed in an easily accessible compartment that is remote from the moving scanner head.

Another feature of the invention is the development of a scanning system that employs an optical fiber to transmit light from a light source to the moving sensor head and relaying optical signals back through an optical fiber to a detector system for signal processing. Both the light source and detector system are located in an off-system site. In view of the spectral nature of the measurement and the mechanical properties of the optical fiber, disturbances to the orientation and/or configuration of the optical fiber can adversely affect the spectral content of light returning to the detector system. This will perturb the measurements. For example, changes to the net bent length of the optical fiber through the introduction or removal of bends during the scanning process can cause changes to optical power, e.g., losses or attenuation, and/or to the tensile stresses of the optical fibers. The optical losses due to bending an optical fiber have a wavelength dependence which will adversely affect any spectroscopic system.

The present invention provides a practical way of controlling the optical fiber path that is connected to a moving scanner head through a series of bends that do not change in number, diameter, or length. In this fashion, the scanning system yields precise and consistent measurements of one or more characteristics of a moving sheet or web.

In one embodiment, the invention is directed to a scanning mechanism, for moving an optical device from a first end to a second end along a main scanning direction, that includes:
  a first stationary turning pulley that is positioned adjacent the first end of the main scanning direction;
  a second stationary turning pulley that is positioned adjacent the second end of the main scanning direction;
  a cable that is partially wound around the first and second stationary pulleys, wherein the cable has a first end that is secured and a second end that is secured;
  a mobile optical device which is operatively connected to the cable between the first and second stationary turning pulleys;
  means for maintaining substantially the same total bend length and radius as the mobile optical device moves along the main scanning direction;
  means for maintaining substantially the same tension on the cable as the mobile optical device moves along the main scanning direction; and
  means for driving the mobile optical device along the main scanning direction.

In another embodiment, the invention is directed to a scanning sensor system, for detecting characteristics on a sheet of material along a main scanning direction, that includes:
  a light source;
  a first stationary turning pulley that is positioned adjacent the first end of the main scanning direction;
  a second stationary turning pulley that is positioned adjacent the second end of the main scanning direction;

an optical fiber cable that is partially wound around the first and second stationary pulleys, wherein the optical fiber cable has a first end that is secured and a second end that is secured;

a mobile optical device which is operatively connected to the optical fiber cable between the first and second stationary turning pulleys so that light from the light source is transmitted to the optical device through the optical fiber cable and signals from the sheet of material is transmitted through the optical fiber cable;

means for maintaining substantially the same tension on the optical fiber cable as the mobile optical device moves along the main scanning direction;

means for driving the mobile optical device along the main scanning direction; and means for converting signals from the optical device into measurements of detected characteristics on the sheet of material.

In a further embodiment, the invention is directed to a method of transmitting radiation from a remote stationary radiation source through a moving optical fiber cable to a scanning optical device and transmitting measured signals from the scanning optical device through the moving optical fiber cable to a remote stationary signal receiving device, said method including the steps of:

(a) providing a scanning system that comprises:
  (i) a first stationary turning pulley;
  (ii) a second stationary turning pulley that is spaced apart from the first stationary turning pulley to define a scanning path for the scanning optical device and wherein the first and second stationary turning pulleys are adapted to support an optical fiber cable along the scanning path; and
  (iii) a tension compensating mechanism for maintaining the tension that is applied to a cable that is looped around the first and second stationary turning pulleys;

(b) looping an optical fiber cable partially around the first and second stationary pulleys and engaging the optical fiber cable to the tension compensating mechanism so that a portion of the optical fiber cable between the first and second stationary turning pulleys define a substantially linear path;

(c) securing a first end of the optical fiber cable;

(d) securing a second end of the optical fiber cable so that the curvature of the optical fiber cable and the total bend length of the optical fiber from the first end to the second end are essentially kept constant as the optical device traverses between the first end and second end;

(e) operatively connecting an optical device to the optical fiber cable between the first and second stationary turning pulleys;

(f) driving the optical device back and forth along the scanning path characterized in that substantially the same tension on the optical fiber cable is maintained while the optical device is scanning;

(g) transmitting radiation from the remote radiation source through a portion of the optical fiber cable to the optical device as the optical device is scanning; and (h) transmitting measured signals from the scanning optical device through the moving optical fiber cable to the remote stationary signal receiving device.

DETAILED DESCRIPTION OF PREFERRED EMBODIMENTS

Figure 1A:
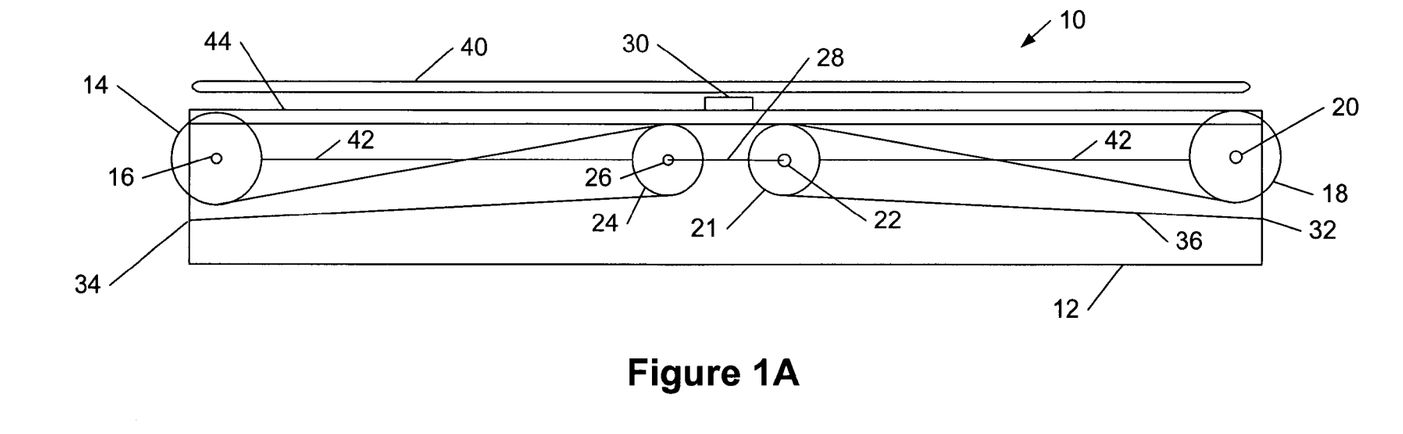
FIGS. 1A and 1B are side schematic views of a cable take-up mechanism.

FIG. 1A illustrates an embodiment of the cable take-up mechanism 10 of the present invention which includes a frame 12 that is constructed of steel or other material(s) of sufficient structural strength. Typically, for scanning systems that are employed to scan in the cross direction of a moving sheet or web 40, the length of the frame 12 is about the same as the width of the moving sheet 40 so that the scanner head 30 is able to traverse the entire width along the cross direction. This distance can be six to eight meters or more. Located on one side of the frame 12 is a first fixed turning pulley 14 which is secured to the frame by pin 16. Positioned on the other side of the frame is second fixed turning pulley 18 which is secured by pin 20. The distance between pins 16 and 20 preferably range from 2 to 12 meters. The diameters of the two fixed turning pulleys 14, 18 are preferably the same. Each pulley preferably has a groove around its outer perimeter that is dimensioned to accommodate a flexible cable.

Situated within the frame 12 and positioned between the two fixed pulleys 14, 18 are a pair of movable or translating pulleys 21, 24 that are linked to each other by a rigid member 28. The pair of movable pulleys 21, 24 are secured by pins 22 and 26, respectively, to a rail 42 which allows the movable pulleys 21, 24 to move back-and-forth along a linear path between the fixed turning pulleys 14, 18. Preferably, the diameters of the movable pulleys 21 and 24 are the same but they are preferably smaller than the diameters of the fixed turning pulleys 14, 18. The centers of the four pulleys 14, 18, 21 and 24 are preferably aligned along a horizontal axis.

An optical fiber cable 36 is partially wound around the four pulleys 14, 18, 21 and 24 as shown. The two ends of the cable 32 and 34 are secured to the frame 12 or other stationary structure. The optical fiber cable 36 should be secured with sufficient tension to avoid excessive slack. No spring or other tension device is needed to secure the two ends. The scanner head 30 is operatively connected to the cable 36 as it scans back and forth along the cross direction between the sides of the moving sheet 40. The linked translating pulleys 21, 24 move in the opposite direction to that of scanner head 30 but travels at half the speed. In this fashion, the cable 36 remains taut throughout from one end 32 to the other end 34 even when the scanner head 30 is in motion. In another embodiment, it is recognized that as the take-up mechanism operates over time, a certain amount of creep may develop in the cable. Thus, the take-up mechanism can be equipped with a spring or other tension device at one or both ends 32 and 34. This will prevent the cable from exhibiting excessive slack. Alternatively, the spring can be positioned in another part of the take-up mechanism such as between the pair of movable pulleys 21, 24. In this case, instead of being connected by a rigid member 28, a member with a spring device can be employed to connect the two of movable pulleys 21, 24.

Figure 1B:
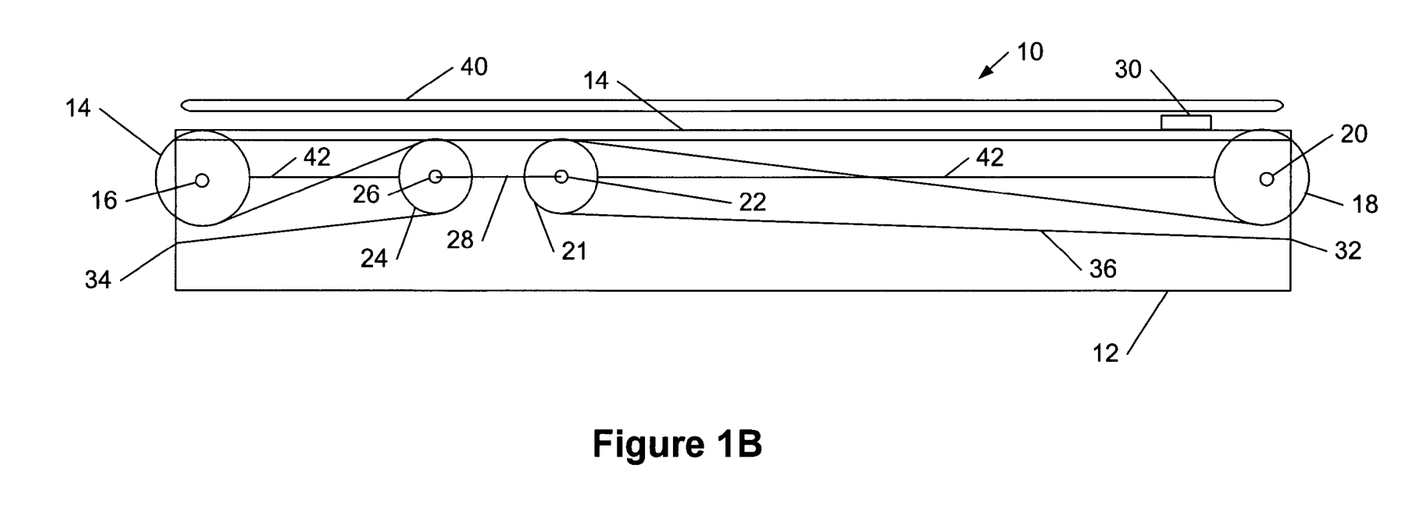
Figures 3, 4:
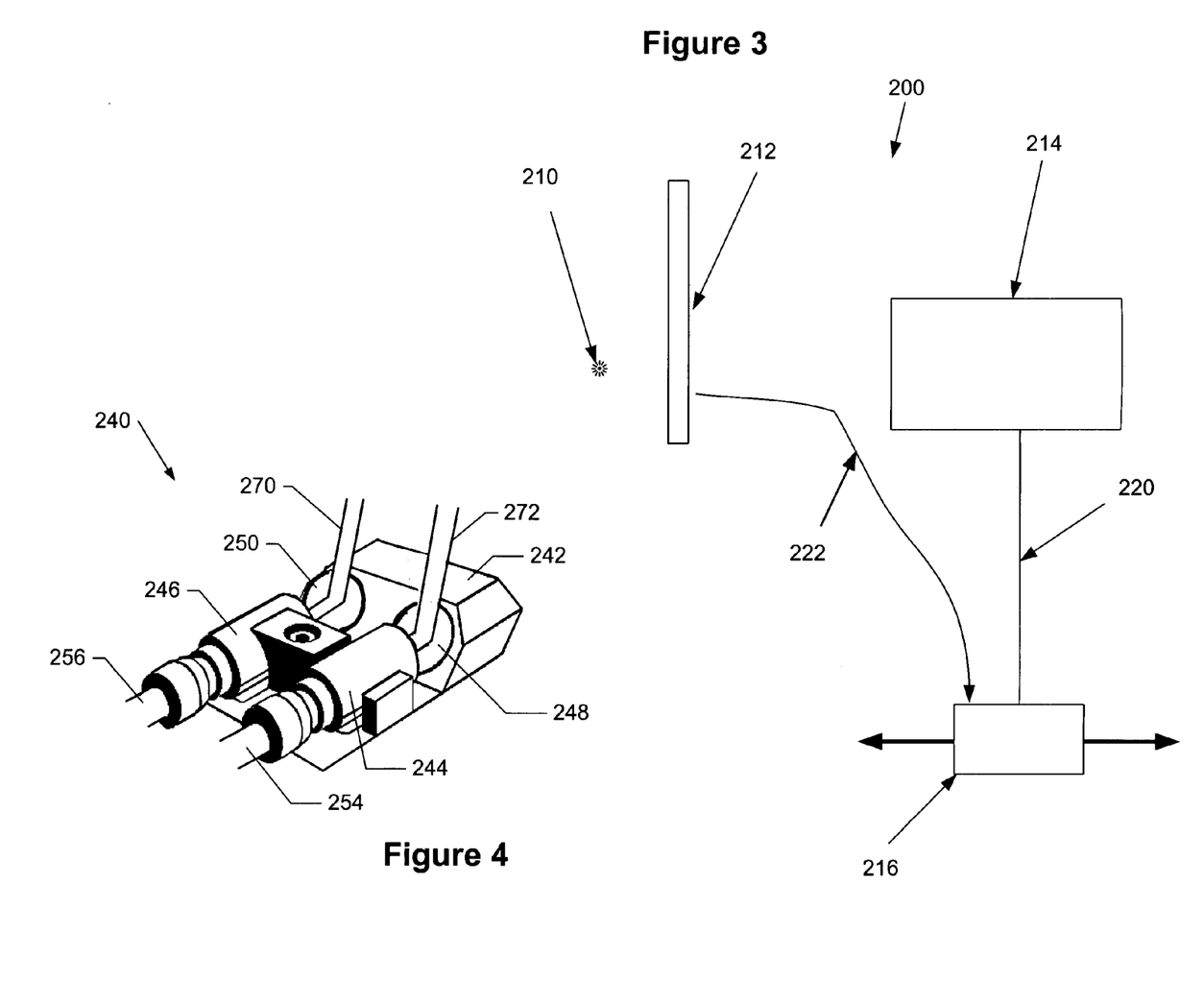
FIG. 3 is a schematic of a scanning system.
FIG. 4 illustrates a sensor head.

As is apparent, in the cable take-up mechanism as shown in FIGS. 1A and 1B, the optical fiber cable is guided around a series of pulleys that determine the bend diameters of the optical fiber cable. Surrounding the optical fiber cable is a tensioned mechanical structure that provides a "loose tube" conduit to support the cable over the width of the scanning distance between the two fixed pulleys 14 and 18 without placing tensile forces on the optical fiber. The set of translating pulleys 22, 26 allows the cable to stay under tension without the need of a spring or a loading device. The translating pulleys, which move in unison, assure that the tension on the cable is maintained essentially constant throughout the cable's length. Movement of the translating pulleys in a direction that is opposite to that of the scanning head 30 serves to distribute the cable in the direction where it is needed in response to the forces that move the scanner head 30 as illustrated in FIG. 3. As illustrated in FIGS. 1A and 1B, as the scanner head 30 moves from one side toward the middle of the cable take-up mechanism 10, reduction in the length of the cable between fixed turning pulley 14 and translating pulley 24 is offset or compensated by a corresponding increase in the length of the cable between fixed turning pulley 18 and translating pulley 21.

With the inventive cable take-up mechanism, the total bend loss as the optical head moves back-and-forth during scanning is preserved. This is important for scanners that use a spectroscopic sensor that measures the relative powers in two or more different wavelength bands. Bend loss in an optical fiber depends upon bend radius and total bend length. If the bend length or the bend radius changes as the mobile optical head is scanned, measurement errors will be introduced. The cable take-up mechanism keeps the angular bend length and the bend radius constant even as the optical head is moving, this in turn minimizes any sensor error. (Note however that the bend positions are changing.) The bend length for the optical fiber is analogous to the length of an arc, which is a segment of a circle. The bend length for an arc is equal to the product of the diameter and the angle between two radii as measured in degrees radian. Thus, an arc that spans 90 degrees has twice the bend length as an arc with the same radius that spans only 45 degrees. The cable take-up mechanism maintains the same total bend length during scanning.

Figure 2:
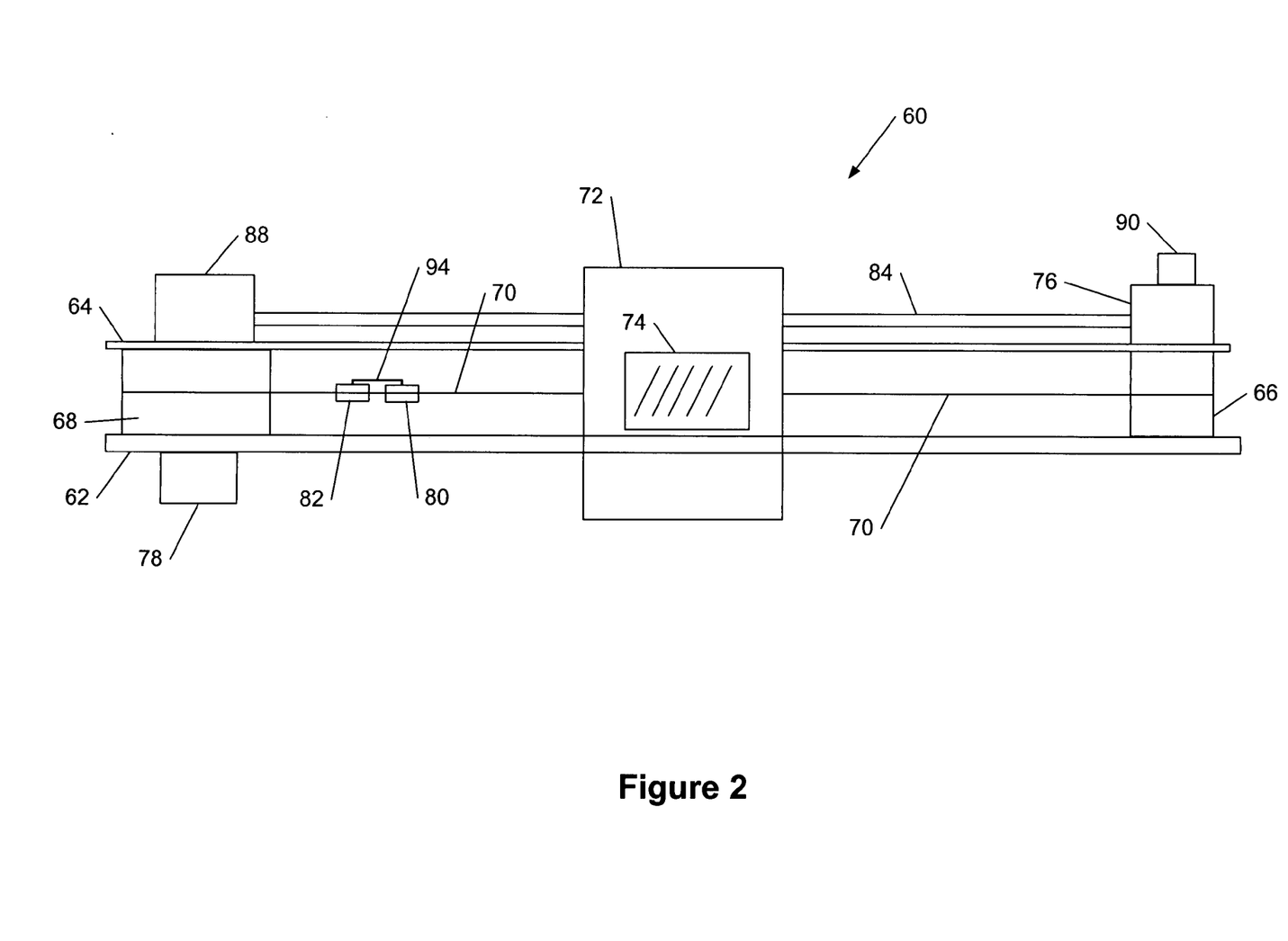
FIG. 2 is a top plan schematic view of a cable take-up mechanism.

The scanner head 30 can be advanced back and forth along the cross direction by a number of mechanisms. In one embodiment, as illustrated in FIG. 2, the cable take-up mechanism 60 includes rails 62 and 64, fixed turning pulleys 66 and 68, and a pair of moving pulleys 80 and 82, which are linked by a rod 94. A carriage 72 rests on top of the rails 62, 64 which function as low-friction guides for the carriage 72 as it travels back and forth. The carriage 72, which can be a platform with rollers, supports scanner head 74. In this arrangement, the scanner head 74 is positioned underneath a web to be analyzed, however, it is understood that the cable take-up mechanism 60 can be employed so that the scanner head 74 is directly above or, at angle relative to, the web to measure properties from its top surface.

In a preferred embodiment, the scanner head 74 houses all or most of the optical elements while the detection electronics are housed in a stationary compartment 78. Thus, measurements are transmitted from the scanner head 74 through cable 70 to the compartment 78. The carriage 72 is connected to a belt 84 that is wound around drive pulley 76 and driven pulley 88 which is operatively connected to motor 90. In operation, control of motor 90 regulates the speed and direction of the movement of the carriage 72.

Alternatively, the belt 84 can be secured directly to the rod 94 which links the pair of movable pulleys 80, 82. In this fashion, activation of the motor 90 also moves the cable 70. As another alternative, the motor 90 can be operatively connected to the fixed turning pulley 66 to drive the scanner head 74.

The inventive cable take-up mechanism can be employed in scanning systems that measure a variety of web or sheet properties. While the scanning system is described with respect to measuring fibrous sheets in a papermaking machine, it is understood that the scanning system can be employed to measure properties of other materials, including, for example, plastics. In the art of making paper with modern high-speed machines, sheet properties must be continually monitored and controlled. The sheet variables that are most often measured include basis weight, moisture content, and caliper, i.e., thickness, of the sheets at various stages in the manufacturing process. Papermaking devices are well known in the art and are described, for example, in Handbook for Pulp & Paper Technologists 2nd ed., G. A. Smook, 1992, Angus Wilde Publications, Inc., and Pulp and Paper Manufacture Vol III (Papermaking and Paperboard Making), R. MacDonald, ed. 1970, McGraw Hill. Sheetmaking systems are further described, for example, in U.S. Pat. No. 5,539,634 to He, U.S. Pat. No. 5,022,966 to Hu, U.S. Pat. No. 4,982,334 to Balakrishnan, U.S. Pat. No. 4,786,817 to Boissevain et al., and U.S. Pat. No. 4,767,935 to Anderson et al. which are incorporated herein by reference. Process control techniques for papermaking machines are further described, for instance, in U.S. Pat. No. 6,149,770 to Hu et al., U.S. Pat. No. 6,092,003 to Hagart-Alexander et. al, U.S. Pat. No. 6,080,278 to Heaven et al., U.S. Pat. No. 6,059,931 to Hu et al., U.S. Pat. No. 6,853,543 to Hu et al., and U.S. Pat. No. 5,892,679 to He, which are all incorporated herein by reference.

FIG. 3 illustrates the sensor layout of a representative scanning system that can be employed to measure the moisture content or other physical properties of a fibrous sheet in the papermaking machine. The scanning system 200 includes a light source 210, optical modulator 212, detector electronics 214, and sensor head 216 which moves back-and-forth along in a linear path adjacent the fibrous sheet. In operation, modulated light from the light source is delivered through a source beam optical fiber 222 to the sensor head 216 where it is focused onto a fibrous sheet. Light that is scattered back from the fibrous sheet is captured by the sensor head 216 and is delivered to the detection electronics 214 via a detector beam optical fiber 220. When measuring sheet properties, the scanning head 216 preferably moves back and forth at a speed of about 0.1 to 50 meters per sec.

Infrared spectroscopy is a preferred technique for moisture content measurements. One approach for single sided IR measurements is to predetermine absorption and reference wavelengths of interest and create a very low resolution spectrometer using band-pass filters and detectors for each channel at the wavelengths of interest. In this regard, the light source 210 provides a constant, reliable, stream of energy within the wavelengths required by the measurement. Moisture measurements typically utilized radiation at wavelengths that yield suitable water absorption peaks.

A number of different sources can be employed for generating radiation at the prerequisite wavelengths including: (1) quartz tungsten halogen (QTH) lamps, (2) IR light emitting diodes, (3) IR laser diodes, and (4) MicroElectroMechanical-Systems (MEMS) IR sources. QTH lamps are preferred given their versatility, reliability, and low costs. When employing a QTH source, a preferred modulation technique is to directly amplitude modulate using the conventional tuning forks or chopper wheel modulation.

Optical fiber cables suitable for the inventive take-up mechanism can comprise commercially available light-transmitting fiber optic cables. However, it should be understood that while the take-up mechanism is particularly suited for routing optical fibers, the mechanism can be employed as a guide for any type of moving cable which is intended to refer to any elongated, flexible material. Cables include, for example, metal wires, ropes, and the like.

Optical fiber cables have a core with an index of refraction that is somewhat greater than the refractive index of the surrounding cladding. A preferred optical fiber, which is available from 3M of St. Paul Minn. under part number FG-550-LER, has a silica core with a silica cladding. The cable has a fluoroacrylate polymer coating that surrounds the silica cladding and an exterior poly(ethylene-co-tetrafluoroethylne) coating as well. In this fiber the primary light guiding interface is defined by the silica/silica core/cladding interface, however, extra light transmission is also achieved by the silica/fluoroacrylate polymer coating interface. In another embodiment, the optical fiber or the polymer-cladded optical fiber can be surrounded by a strong non-collapsing tubing of a suitable material such as PEEK which is commercially available from TexLoc Ltd. The optical fiber sits loosely within this PEEK tubing. The fiber PEEK tubing structure is then surrounded by an inelastic or non-stretch material in the form of a rope, for instance. A suitable material is a high-strength fiber that is commercial available as VECTRAN from Celanese Corporation. By applying tension on the exterior rope, the optical fiber can move freely or "float" within the rope.

Optical fibers having high numerical apertures can also be employed. Typically, these optical fibers have a numerical aperture that ranges from 0.1 to about 0.37 to 0.48 or higher. The numerical aperture is a function of the optical properties and in particular the index of refraction difference between the core and the cladding of the optical fiber. The numerical aperture creates a cone of acceptance for the fibers. Accordingly, light emanating from the fibers may occur anywhere within the region defined by the cone of acceptance. Likewise, light entering the acceptance cone will also enter the fibers. Optical fibers with high numerical aperture are described in U.S. Pat. No. 5,170,056 to Berard which is incorporated herein by reference. These large numerical aperture optical fibers are less sensitive to optical losses due to bending and therefore their employment affords more robust measurements.

As shown in FIGS. 1A and 1B, the cable configuration of the take-up mechanism has bends. Some of the bends will be stationary in that their lengths, forms and positions will not change after installation and during operation. Non-stationary bends are bends that that do change their positions on relatively short time scales on the order of less than 1 ms to several minutes; these are the kinds of bends that will be induced while scanning. The scanning system employing the take-up mechanism is capable of maintaining calibration and specification when the bend spectrum changes in these situations. It has been shown that increasing the number of bends will increase the amount of light that is lost while being transmitted through a optical fiber. To minimize losses associated with fiber disturbance, the bend radius of the stationary bends should be kept larger than the minimum bend radius for a particular design. The minimum fiber bend radius for a particular optical fiber cable design is specified by the manufacturer.

The sensor head 216 comprises a suitable optical head that is connected to both the source beam optical fiber cable 222 and detector beam optical fiber cable 220 as shown in FIG. 3. As shown in FIG. 4, a suitable optical head 240 comprises a body 242 with couplers 244 and 246 for connecting the source beam and detector beam optical fiber cables 254 and 256, respectively. The sensor head may optionally comprise a housing enclosing the optical head 240 from the environment.

Light 270 delivered from the optical fiber cable 254 is reflected from a turning mirror 250 and onto the sheet or web being scanned. Appropriate focusing lenses (not shown) can be employed. Scattered light 272 from the sheet is reflected from the mirror 248 and into the detector beam optical fiber cable 256. The contours of mirrors 250 and 248 can be fashioned so that light can be focused onto and captured from appropriate orientations relative to the moving sheet being scanned. The mirrors can comprise a layer of gold, silver, aluminum, dielectric or other suitable reflective material.

The embodiment of the optical head 240 in FIG. 4 is connected to the ends of two fiber optic cables 254, 256. This design permits light from the light source and light scattered from the sheet of being analyzed, that is relayed to the signal processing components of the detector system, to be transmitted through a different parts of the cable. However, it is known that light from the light source and light scattered from the sheet can be transmitted through the same part of the cable. In this latter case, the optical head 240 would only need to be connected to the end of one fiber optical cable.

The optical head 240 as shown in FIG. 4 is part of a mobile optical device that moves back and forth during scanning measurement. To minimize the power needed to move the scanner head, the optical device should be light weight. Accordingly, it is preferred that the number of components that comprise the mobile optical device be kept to a minimum as well. In one embodiment, the mobile optical device includes an optical element such as the optical head 240 that delivers light to a moving sheet and relays scattered light from the sheet. The light source and other device of the detection system such as the signal processing components are located elsewhere that is remote compartment. The mobile optical device should be compact and typically weigh less than 1 kilograms and preferably less than 200 grams.

Spectrometric scanning systems are further described, for instance, U.S. Pat. No. 5,795,394 to Belotserkovsky et al., discloses a scanning reflective-type infrared coating sensor and U.S. Pat. No. 6,404,502 to Preston et al. discloses a reflective-type gloss sensor, both patents are incorporated herein by reference. On-line scanning sensor systems for optically measuring the dry basis weight, basis weight, and moisture content of fibrous sheets during papermaking manufacture are disclosed in U.S. Pat. No. 4,879,471 to Dahlquist, U.S. Pat. No. 5,094,535 to Dahlquist et al., and U.S. Pat. No. 5,166,748 to Dahlquist, all of which are incorporated herein by reference.

Figure 5A:
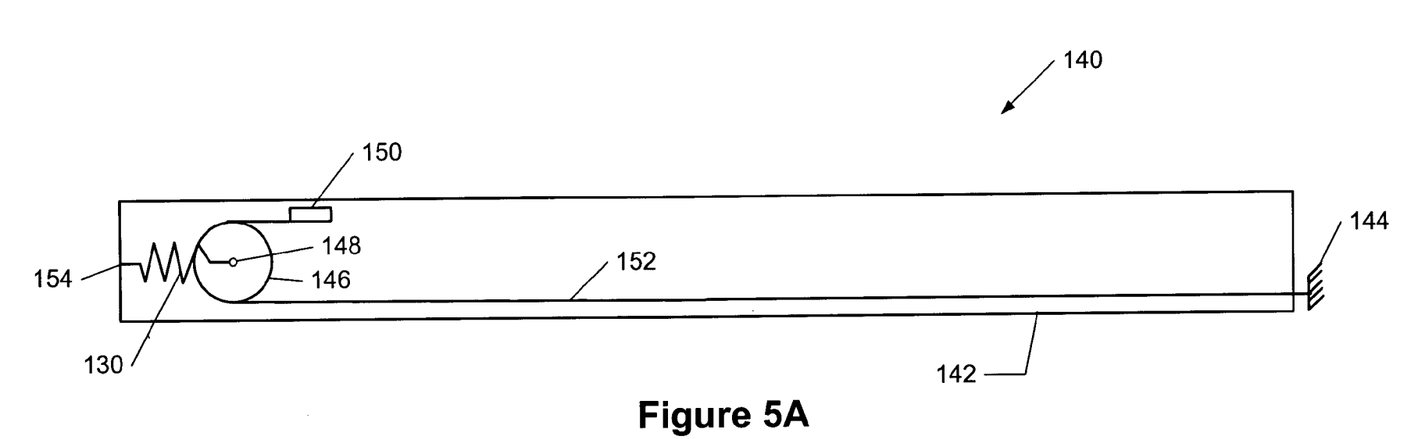
FIGS. 5A and 5B are side schematic views of another embodiment of a cable take-up mechanism.
Figure 5B:
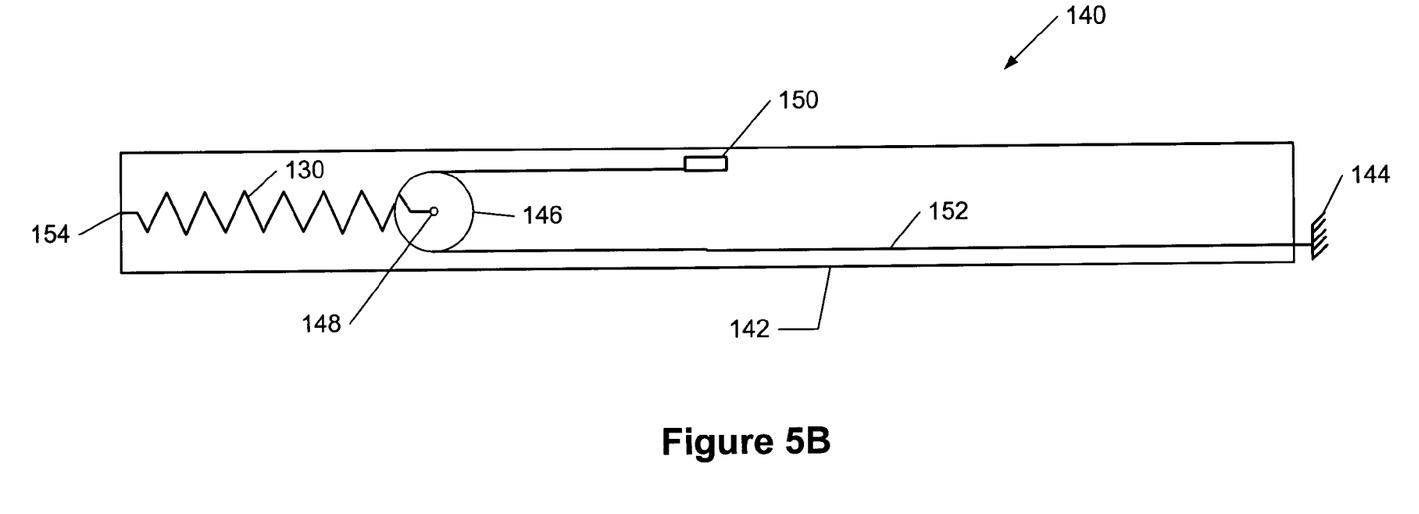

FIGS. 5A and 5B illustrates another embodiment of a cable take-up mechanism 140 which includes a frame 142 and a movable turning pulley 146. One end of cable 152 is secured to one end at position 144 while the other end of the cable is attached to scanner head 150. The pulley 146 is secured at its center with pin 148 which can be supported by a rail (not shown) that runs parallel to the linear path of the scanner head. The pulley 146 is secured by a tension device 130, e.g., spring, at position 154. The scanner head 150 can be driven by a suitable motor as described above. The cable 152 is wound around the pulley 146 so that as the scanner head 150 is pulled towards the center of the mechanism 140, the tension device imparts a sufficient force to keep the cable 152 from slacking.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A scanning mechanism for moving a mobile optical device between a first end and a second end along a main scanning direction that comprises:
   means for maintaining substantially the same total bend length and radius as the mobile optical device moves along the main scanning direction;
   means for maintaining substantially the same tension on a cable as the mobile optical device moves along the main scanning direction, wherein the optical device is operatively connected to the cable;
   means for driving the mobile optical device along the main scanning direction;
   a first stationary turning pulley that is positioned adjacent the first end of the main scanning direction;
   a second stationary turning pulley that is positioned adjacent the second end of the main scanning direction;
   a cable that is partially wound around the first and second stationary pulleys, wherein the cable has a first end that is secured and a second end that is secured and the mobile optical device that positioned between the first and second stationary turning pulleys, wherein the means for maintaining substantially the same tension, same total bend length and radius on the cable comprises:
   (a) a first compensating pulley; and
   (b) a second compensating pulley, wherein the cable that is partially wound around the first and second compensating pulleys, wherein the first and second compensating pulleys are linked to move in unison along a path that is between the first and second stationary turning pulleys, and wherein the first compensating pulley is closer to the first stationary turning pulley than is the second compensating pulley and wherein the means for driving the mobile optical device moves the mobile optical device in a first direction and simultaneously moves the linked first and second compensating pulleys in a second direction that is opposite to the first direction.

2. The scanning mechanism of claim 1 wherein the first end of the cable is secured to a first side of the scanning mechanism and the cable is partially looped around the first compensating pulley and directed toward the first stationary turning pulley and wherein the second end of the cable is secured to a second side of the scanning mechanism and the cable is partially looped around the second compensating pulley and directed toward the second stationary turning pulley.

3. The scanning mechanism of claim 1 wherein the means for driving the mobile optical device comprises a motor that drives one of the first or second stationary turning pulleys to cause the mobile optical device to scan back and forth along the main scanning direction.

4. The scanning mechanism of claim 1 further comprising a rail that is positioned so that the length of the rail is parallel to the axis of the main scanning direction and wherein the mobile optical device is supported by the rail in traveling back and forth along the main scanning direction.

5. The scanning mechanism of claim 1 further comprising a carriage that is supported by a rail that is positioned so that the length of the rail is parallel to axis of the main scanning direction and wherein the mobile optical device is attached to the carriage.

6. The scanning mechanism of claim 5 further comprising a drive pulley, an idler pulley, a drive motor, and a belt that is operatively connected to the carriage.

7. The scanning mechanism of claim 1 wherein the diameters of the first and second stationary turning pulleys are substantially the same and they are larger than those of the first and second compensating pulleys.

8. The scanning mechanism of claim 7 wherein the center of the first stationary turning pulley, center of the second stationary turning pulley, center of the first compensating pulley and the center of the second compensating pulley are aligned on the same axis.

9. The scanning mechanism of claim 1 wherein the distance between the first and second compensating pulleys remains fixed.

10. The scanning mechanism of claim 9 wherein the first and second compensating pulleys are linked together by a rigid member.

11. The scanning mechanism of claim 10 further comprising an elongated guide with a length that runs parallel to the axis of the main scanning direction and wherein the rigid member is slideably attached to the guide.

12. The scanning mechanism of claim 1 wherein the mobile optical device moves at a speed of 0.1 to 50 m/s.

13. The scanning mechanism of claim 1 wherein the mobile optical device comprises one or more optical elements.

14. The scanning mechanism of claim 13 wherein the optical device is an optical head having a mass of less than about 200 grams.

15. The scanning mechanism of claim 1 wherein the distance between the center of the first stationary pulley and the center of the second stationary pulley is about 2 to 12 meters.

16. The scanning mechanism of claim 1 wherein each of the first and second turning pulleys and of first and second compensating pulleys has a peripheral groove dimensioned for receiving a portion of the cable.

17. The scanning mechanism of claim 1 wherein the cable is not connected to a spring or loading mechanism.

18. A scanning sensor system for detecting characteristics on a sheet of material along a main scanning direction that comprises:
   a light source;
   a first stationary turning pulley that is positioned adjacent the first end of the main scanning direction;
   a second stationary turning pulley that is positioned adjacent the second end of the main scanning direction;
   an optical fiber cable that is partially wound around the first and second stationary pulleys, wherein the optical fiber cable has a first end that is secured and a second end that is secured and wherein the curvature and total bend length of the optical cable along its entire length from the first end to the second end are kept essentially the same while a mobile optical device traverses between the first and second ends;
   a mobile optical device that is operatively connected to the optical fiber cable between the first and second stationary turning pulleys so that light from the light source is transmitted to the optical device through the optical fiber cable and signals from the sheet of material is transmitted through the optical fiber cable;
   means for maintaining substantially the same tension on the optical fiber cable as the mobile optical device moves along the main scanning direction;
   means for driving the mobile optical device along the main scanning direction; and
   means for converting signals from the optical device into measurements of detected characteristics on the sheet of material.

19. The scanning system of claim 18 wherein optical device transmits spectroscopic signals from the sheet of material.

20. The scanning system of claim 18 wherein the sheet of material is a moving web and the optical device traverses in the cross direction relative to the direction of the moving web.

21. The scanning system of claim 20 wherein the moving web comprises wet stock or paper of a papermaking machine.

22. The scanning system of claim 18 wherein the light source generates infrared radiation.

23. The scanning system of claim 18 wherein the optical device is positioned above the sheet of material.

24. The scanning system of claim 18 wherein the optical device is positioned below the sheet of material.

25. A method of transmitting radiation from a remote stationary radiation source through a moving optical fiber cable to a scanning optical device and transmitting measured signals from the scanning optical device through the moving optical fiber cable to a remote stationary signal receiving device, said method comprising the steps of:
   (a) providing a scanning system that comprises:
      (i) a first stationary turning pulley;
      (ii) a second stationary turning pulley that is spaced apart from the first stationary turning pulley to define a scanning path for the scanning optical device and wherein the first and second stationary turning pulleys are adapted to support an optical fiber cable along the scanning path; and
      (iii) a tension compensating mechanism for maintaining the tension that is applied to a cable that is looped around the first and second stationary turning pulleys;
   (b) looping an optical fiber cable partially around the first and second stationary pulleys and engaging the optical fiber cable to the tension compensating mechanism so that a portion of the optical fiber cable between the first and second stationary turning pulleys define a substantially linear path;
   (c) securing a first end of the optical fiber cable;
   (d) securing a second end of the optical fiber cable so that the curvature of the optical fiber cable and the total bend length of the optical fiber from the first end to the second end are essentially kept constant as the optical device traverses between the first end and second end
   (e) operatively connecting an optical device to the optical fiber cable between the first and second stationary turning pulleys;
   (f) driving the optical device back and forth along the scanning path characterized in that substantially the same tension on the optical fiber cable is maintained while the optical device is scanning;
   (g) transmitting radiation from the remote radiation source through a portion of the optical fiber cable to the optical device as the optical device is scanning; and
   (h) transmitting measured signals from the scanning optical device through the moving optical fiber cable to the remote stationary signal receiving device.

26. The method of claim 25 wherein step (f) comprises driving the optical device back and forth along a horizontal path that is substantially equidistance from a sheet of material.

27. A scanning mechanism for moving a mobile optical device between a first end and a second end along a main scanning direction that comprises:
   means for maintaining substantially the same total bend length and radius as the mobile optical device moves along the scanning direction;
   means for maintaining substantially the same tension on a cable as the mobile optical device moves along the scanning direction, wherein the optical device is operatively connected to the cable;
   means for driving the mobile optical device along the main scanning direction;
   a first stationary turning pulley that is positioned adjacent the first end of the main scanning direction;
   a second stationary turning pulley that is positioned adjacent the second end of the main scanning direction; and
   a cable that is partially wound around the first and second stationary pulleys, wherein the cable has a first end that is secured and a second end that is secured and the mobile optical device that is positioned between the first and second stationary turning pulleys wherein the cable is an optical fiber cable.

28. The scanning mechanism of claim 27 wherein the optical fiber cable has a numerical aperture of at least 0.1.

* * * * *